(12) United States Patent
Shimada et al.

(10) Patent No.: US 6,726,669 B2
(45) Date of Patent: Apr. 27, 2004

(54) DISPOSABLE PULL-ON GARMENT

(75) Inventors: Takaaki Shimada, Kagawa-ken (JP);
Kenji Nakamura, Kagawa-ken (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/975,189

(22) Filed: Oct. 12, 2001

(65) Prior Publication Data

US 2002/0045877 A1 Apr. 18, 2002

(30) Foreign Application Priority Data

Oct. 13, 2000 (JP) .......................... 2000-314189

(51) Int. Cl.$^7$ .......................... A61F 13/15; A61F 13/20
(52) U.S. Cl. .......................... 604/385.29; 604/385.28; 604/396
(58) Field of Search .......... 604/385.22, 385.24–385.31, 604/392–398

(56) References Cited

U.S. PATENT DOCUMENTS

| | | | | |
|---|---|---|---|---|
| 5,415,649 A | * | 5/1995 | Watanabe et al. | 604/385.29 |
| 5,554,143 A | * | 9/1996 | Roe et al. | 604/385.3 |
| 5,916,206 A | * | 6/1999 | Otsubo et al. | 604/385.27 |
| 5,941,865 A | * | 8/1999 | Otsubo et al. | 604/385.29 |
| 6,264,643 B1 | * | 7/2001 | Toyoda | 604/385.29 |
| 2002/0045872 A1 | * | 4/2002 | Shimada et al. | 604/385.3 |
| 2002/0049421 A1 | * | 4/2002 | Hayase et al. | 604/385.27 |

FOREIGN PATENT DOCUMENTS

| | | | | |
|---|---|---|---|---|
| EP | 753292 A2 | * | 1/1997 | A61F/13/15 |
| EP | 0761194 | | 12/1997 | |
| EP | 1300124 A2 | * | 4/2003 | A61F/13/496 |
| GB | 2266445 | | 3/1993 | |
| JP | 4-371147 A | * | 12/1992 | |
| JP | 4-371148 A | * | 12/1992 | |
| JP | 7-236650 | | 9/1995 | |
| JP | 2002253605 A | * | 9/2002 | A61F/13/49 |

OTHER PUBLICATIONS

Patent Abstracts of Japan, vol. 1996, No. 01, Jan. 31, 1996 & JP 07 236650 A (Toyoeizaki KK), Sep. 12, 1995.

* cited by examiner

Primary Examiner—Karin Reichle
(74) Attorney, Agent, or Firm—Lowe Hauptman Gilman & Berner LLP

(57) ABSTRACT

A disposable pull-on garment includes front and rear waist-encircling regions each having first elasticized zones and a second elasticized zone extending in a waist-encircling direction. Auxiliary elastic members include plural lines of first auxiliary elastic members extending in the waist-encircling direction in the first elasticized zones, and plural lines of second auxiliary elastic members extending in the waist-encircling direction in the second elasticized zones. A tensile stress of the first auxiliary elastic members is greater than that of the second auxiliary elastic members. A tensile stress of the first elasticized zones is greater than that of the second elasticized zone.

17 Claims, 7 Drawing Sheets

DISPOSABLE PULL-ON GARMENT

BACKGROUND OF THE INVENTION

This invention relates to a disposable pull-on garment which absorbs and retains excrements.

Japanese Patent Application Publication No. 1995-236650A discloses a disposable pull-on diaper which comprises a liquid pervious top sheet, a liquid impervious back sheet and a liquid absorbent core interposed between those two sheets, with respective longitudinal side edges of front and rear waist-encircling regions being secured to each other to provide a waist-encircling opening and a pair of leg-encircling openings. In the front waist-encircling region, a plurality of waist elastic members extending in a waist-encircling direction are secured in an extended state to an edge portion of the waist-encircling opening. To an edge portion of each leg-encircling opening, a plurality of leg elastic members are secured in an extended state extending in a leg-encircling direction. Also, a plurality of auxiliary elastic members extending in the waist-encircling direction between the longitudinal side edges of the front and rear waist regions are secured in a region between the waist elastic members and the leg-encircling opening edge portions.

Each auxiliary elastic member has an extensible portion and a non-extensible portion. The extensible portion extends from longitudinal side edges of the core positioned over the front and rear waist-encircling regions toward respective longitudinal side edges of the front waist-encircling region. The non-extensible portion traverses the core to extend between opposite longitudinal side edges of the core. The extensible portions of the auxiliary elastic members act to tighten a wearer's waist so that the diaper while in use is prevented from sliding down from its position. In the non-extensible portions of the auxiliary elastic members, the diaper is not subjected to a tensile stress from the auxiliary elastic members which may otherwise cause the core to contract, so that the core is prevented from puckering.

The diaper disclosed in the above Publication relies solely on the extensible portions of auxiliary elastic members to prevent its downward slide and accordingly requires an increase in tensile stress of the auxiliary elastic members in their extensible portions. The diaper is thus pressed strongly against the wearer's waist, making the wearer uncomfortable. The non-extensible portions of the auxiliary elastic members do not act to press the core against the wearer's skin. This increases the possibility of the core being spaced from the wearer's skin in use, and accordingly adversely affects the excrement-absorbing function of the core.

SUMMARY OF THE INVENTION

It is an object of this invention to provide a disposable pull-on garment which, in use, is not pressed locally against a waist region of the wearer and does not adversely affect the function of the core to absorb excrements.

The present invention provides a disposable pull-on garment having a waist-encirclable direction and a longitudinal direction orthogonal to the waist-encirclable direction. The garment comprises a liquid-pervious topsheet, a liquid-impervious backsheet and a liquid-absorbent core interposed between the topsheet and backsheet to define front and rear waist-encirclable regions and a crotch region extending between the front and rear waist-encirclable regions. The respective longitudinal side edges of the front and rear waist regions are joined together in the longitudinal direction to define a waist-encirclable opening and a pair of leg-encirclable openings. Waist-encirclable elastic members are attached to respective edge zones of the waist-encirclable opening in the front and rear waist-encirclable regions. There are provided plural lines of auxiliary elastic members, which extend in the waist-encirclable direction and are arranged to be spaced at distances from each other in the longitudinal direction in a region defined between the waist-encirclable elastic members and the leg-encirclable openings in at least one of the front and rear waist-encirclable regions. At least one of the front and rear waist-encirclable regions has first elasticized zones and a second elasticized zone, wherein the second elasticized zone traverses a portion of the core in that region and extends in the waist-encirclable direction between opposite longitudinal side edges of the portion of the core, and wherein the first elasticized zones extend in the waist-encirclable direction outwardly from the longitudinal side edges of the portion of the core, respectively, to the adjacent one of the longitudinal side edges of the associated waist-encirclable region. The auxiliary elastic members include plural lines of first and second auxiliary elastic members, the first auxiliary elastic members being positioned in the first elasticized zones, the second auxiliary elastic members being non-continuous with the first auxiliary elastic members and being positioned in the second elasticized zone. A tensile stress of the first elasticized zone is greater than that of the second elasticized zone.

In accordance with a first aspect of the present invention, a tensile stress of the first auxiliary elastic members is greater than that of the second auxiliary elastic members.

In accordance with a second aspect of the present invention, the number of the first auxiliary elastic members is larger than that of the second auxiliary elastic members.

According to one exemplary embodiment of the present invention, each first elasticized zone when extended to its maximum extent exhibits a tensile stress in a range of 0.2–2.0 N/25 mm, and the second elasticized zone when extended to its maximum extent exhibits a tensile stress in a range of 0.1–0.6 N/25 mm.

DETAILED DESCRIPTION OF THE PREFERRED EMBODIMENTS

A disposable pull-on garment in accordance with the present invention is described below in detail with reference to the attached drawings as is used in a disposable pull-on diaper.

Figure 1:
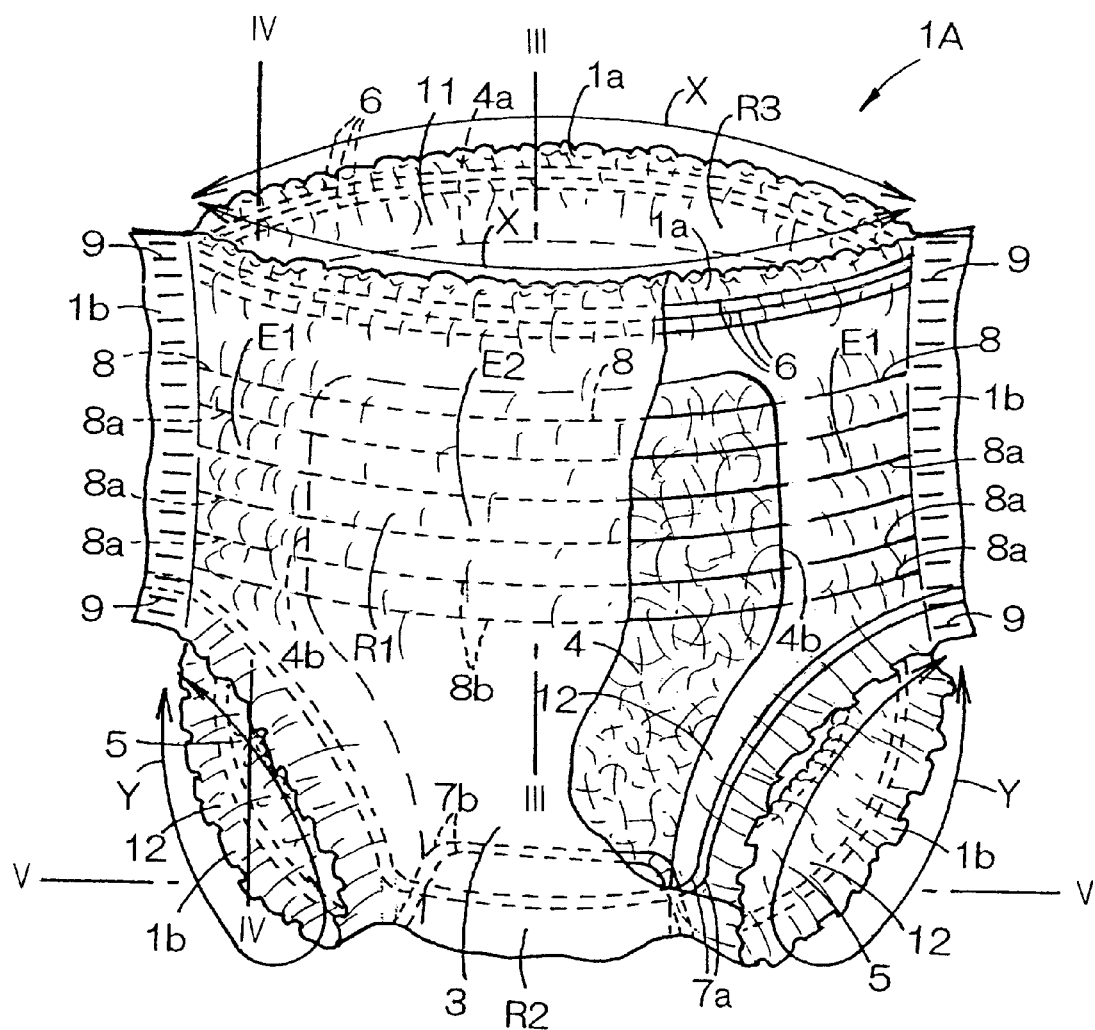
FIG. 1 is a partially cut-away perspective view of a disposable diaper in one exemplary embodiment of the invention.
Figure 2:
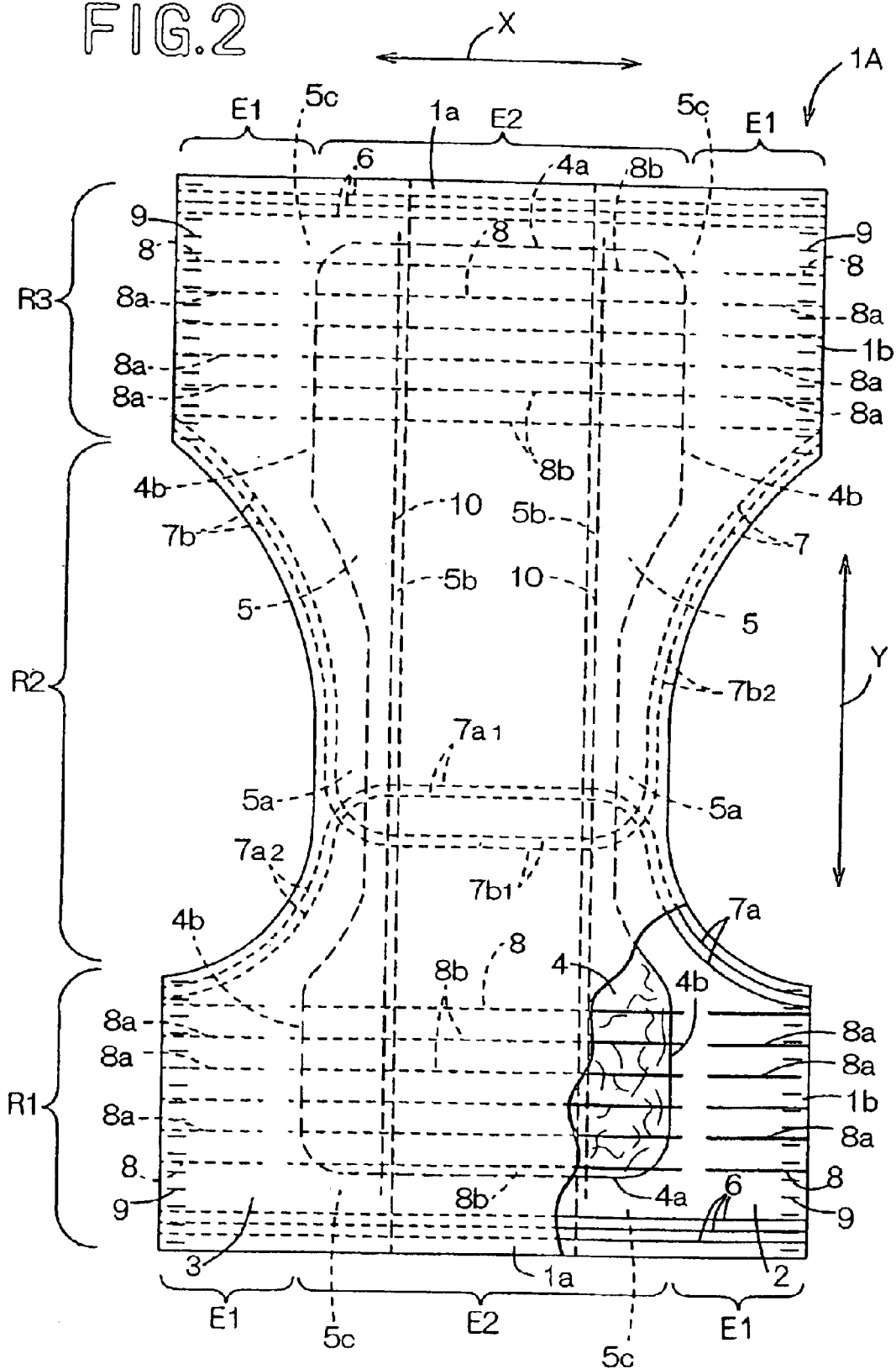
FIG. 2 is a partially cut-away plan view of the diaper when the front and rear waist regions are disconnected from each other and developed longitudinally.

FIG. 1 is a partially cut-away perspective view of an illustrative disposable diaper 1A. FIG. 2 is a partially cut-away plan view of the diaper 1A when its front and rear waist-encircling regions R1, R3 are disconnected from each other and developed in a longitudinal direction. In FIG. 1, a waist-encircling direction is shown by the arrow X and a leg-encircling direction is shown by the arrow Y. In FIG. 2, the diaper 1A is viewed from a side of its back sheet 3. A lateral direction and a longitudinal direction are shown by the arrows X and Y, respectively. An inside surface of the top or back sheet 2, 3 means its surface is positioned to face toward a core 4. An outside surface of the top or back sheet 2, 3 means its surface is positioned away from the core 4.

The diaper 1A comprises as major components a liquid pervious top sheet 2, a liquid impervious back sheet 3, and a liquid-absorbing core 4 interposed between the top and back sheets 2, 3 and wrapped entirely by and joined to tissue paper (not shown), and substantially liquid impervious, leakage-resistant cuffs 5. The core 4 is joined via the tissue paper to inner surfaces of the top and back sheets 2 and 3.

The diaper 1A includes front and rear waist-encircling regions R1 and R3 opposed to each other, and a crotch region R2 positioned between the front and rear waist-encircling regions R1, R3. A waist-encircling opening 11 and a pair of leg-encircling openings 12 are defined in the diaper 1A.

As shown in FIG. 2, the diaper 1A has laterally-extending end edges 1a and longitudinally-extending side edges 1b. Each of the side edges 1b in the crotch region R2 describes a line curved laterally inward of the diaper 1A.

A plurality of laterally-extending waist elastic members 6 are secured in an extended state along end edges 1a. In the crotch region R2, a plurality of leg elastic members 7 are secured in an extended state along side edges 1b. In each of the front and rear waist-encircling regions R1 and R3, a plurality of auxiliary elastic members 8 extending laterally and spaced longitudinally from each other at a pre-determined distance are secured in an extended state in a region between the waist and leg elastic members 6 and 7.

The diaper 1A is of a pull-on type wherein opposite side edges 1b in the front and rear waist-encircling regions R1 and R3 overlay each other and are secured to each other at plural joints 9 intermittently arranged along the longitudinal direction.

In the diaper 1A, the end edges 1a of the diaper 1A in FIG. 2 define an edge portion 1a of the waist-encircling opening 11, and the side edges 1b of the diaper 1A in FIG. 2 define respective edge portions 1b of the leg-encircling openings 12 in the crotch region R2, as shown in FIG. 1. The waist elastic members 6 extend in the waist-encircling direction in the edge portion 1a of the waist-encircling opening 11. The leg elastic members 7 extend in the leg-encircling direction along the edge portions 1b of each of leg-encircling openings 12. The auxiliary elastic members 8 extend in the waist-encircling direction in an area located between the waist elastic members 6 and the edge portions 1b of the leg-encircling openings 12.

Each of the front and rear waist-encircling regions R1, R3 of the diaper 1A has two first elasticized zones E1 and a second elasticized zone E2. Each first elasticized zone E1 extends in the waist-encircling direction in the region between the vicinity of one of opposite side edges 4b of the core 4 positioned in the front or rear waist-encircling region R1 or R3 and the respective opposite side edge 1b of the front or rear waist-encircling region, R1 or R3. The second elasticized zone E2 traverses the core, extending in the waist-encircling direction between the vicinities of opposite side edges 4b of the core 4.

The auxiliary elastic members 8 include plural lines of first auxiliary elastic members 8a and plural lines of second auxiliary elastic members 8b. The first auxiliary elastic members 8a are spaced longitudinally from each other by a pre-determined distance and extend in the waist-encircling direction in the first elasticized zones E1. The second auxiliary elastic members 8b are spaced longitudinally from each other by a pre-determined distance and extend in the waist-encircling direction in the second elasticized zone E2. The number of the first auxiliary elastic members 8a is equal to that of the second auxiliary elastic members 8b. The tensile stress of each of the first auxiliary elastic members is greater than the tensile stress of each of the second auxiliary elastic members.

In the diaper 1A, the tensile stress of the first elasticized zones E1 is greater than the tensile stress of the second elasticized zone E2. Also in the diaper 1A, each first elasticized zone E1 when extended to its maximum extent exhibits a tensile stress in a range of 0.2–2.0 N/25 mm, preferably in a range of 0.4–1.0 N/25 mm. The second elasticized zone E2 when extended to its maximum extent exhibits a tensile stress in a range of 0.1–0.6 N/25 mm.

The following procedure is utilized to measure tensile stress for the first and second elasticized zones E1 and E2. (1) First, the first elasticized zone E1 is partially cut out to prepare a first test piece and the second elasticized zone E2 is partially cut out to prepare a second test piece. The first test piece includes portions of the first auxiliary elastic members 8a, and has a dimension of 100 mm in the waist-encircling direction and a dimension of 25 mm in the longitudinal direction. The second test piece includes portions of the second auxiliary elastic members 8b (excluding the core 4), and has a dimension of 100 mm in the waist-encircling direction and a dimension of 25 mm in the longitudinal direction. (2) Then, the tensile stress of each test piece is measured using a tensile tester. Prior to the measurement of tensile stress, each test piece must be subjected to contraction by relieving the stress, and then extended by the tensile tester to a size of 100 mm. The tensile stress is a value measured when each test piece is elongated to a maximum size of 100 mm.

In the diaper 1A, the first elasticized zones E1 exhibit a higher tensile stress than the second elasticized zone E2. Accordingly, when the diaper is worn, the first elasticized zones E1 tighten around the wearer's waist more strongly than the second elasticized zone E2. However, in the diaper 1A, the first elasticized zones E1 together with the second elasticized zone E2 tighten around the wearer's waist so as to prevent the diaper 1A from sliding down from its intended position. Thus, the tensile stress of the first elasticized zones E1 in this diaper is not required to be as high as in the prior art diaper so that it is sufficient for the tensile stress to be maintained within the above-specified range.

In the second elasticized zone E2 in the diaper 1A, the second auxiliary elastic members 8b press the core 4 against the wearer's skin by their tensile stress so that the core 4 of the diaper 1A in use is prevented from being spaced from the wearer' skin. As a result, a situation in which the excrement-absorbing function of the core 4 is adversely affected can be avoided. Since the tensile stress of the second elasticized zone E2 in the diaper 1A is maintained within the above-specified range, the core 4 due to its rigidity withstands the force exerted by the second elasticized zone E2 when subjected to contraction and thus wrinkles will not be formed on the core 4.

If the tensile stress of the first elasticized zones E1 is below 0.2 N/25 mm, the pressing force of the first elasticized zones E1 around the wearer's waist becomes weak, increasing a possible tendency of the diaper 1A, to slide down from its intended position. If the tensile stress of the first elasticized zones E1 exceeds 2.0 N/25 mm, the pressing force of the first elasticized zones E1 around the wearer's waist becomes stronger than necessary. This results in a strong pressure on the wearer's waist making the wearer uncomfortable. If the tensile stress of the second elasticized zone E2 is below 0.1 N/25 mm, it may fail to press the core 4 enough against the wearer's skin so that in some occasions, the core 4 is spaced from the wearer's skin. If the tensile stress of the second elasticized zone E2 exceeds 0.6 N/25 mm, the core 4 may have wrinkles when the second elasticized zone E2 contracts and, in some occasions the core 4 is spaced from the wearer's skin.

Each leakage-prevention cuff 5 extends longitudinally along one of the side edges 1b of the diaper 1A. Each cuff 5 has a fixed edge 5a that extends longitudinally adjacent the respective side edge 4b of the core 4, a free edge 5b that is associated with the fixed edge 5a and biased to be spaced from the top sheet 2, fixed ends 5c each folded laterally inwardly to overlay the top sheet 2, and side portion 5d (refer to FIG. 5) that extends from the fixed side edge 5a toward the respective side edge 1b of the diaper 1A. An elastic member 10 is attached in an extended state to the free edge 5b. The elastic member 10 is enclosed in a sleeve portion defined in the free edge 5b.

The leg-encircling elastic members 7 include a first leg elastic member 7a and a second leg elastic member 7b. Each of these leg elastic members 7a and 7b includes a central portion $7a_1$, $7b_1$ that traverses the crotch region R2 and opposite side portions $7a_2$, $7b_2$ that extend along the respective side edges 1b of the diaper. Each side portion $7a_2$ of the first leg elastic member 7a is located in about a front half of the side edges 1b portion that extends in the crotch region R2. Each side portion $7b_2$ of the second leg elastic member 7b is located in about a rear half of the side edge 1b portion that extends in the crotch region R2.

Figure 3:
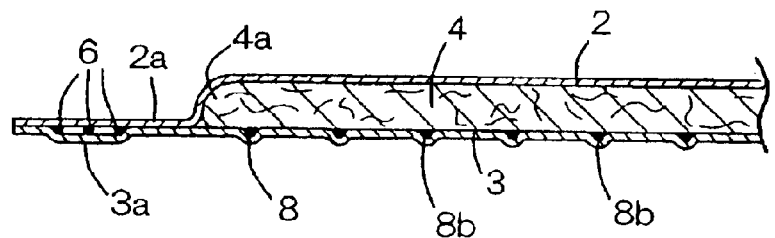
FIG. 3 is a cross-sectional view taken along line III—III of FIG. 1.
Figure 4:
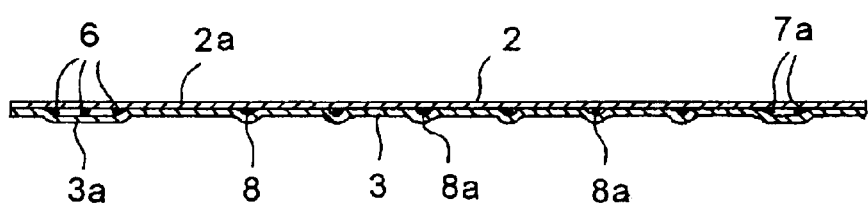
FIG. 4 is a cross-sectional view taken along line IV—IV of FIG. 1.
Figure 5:
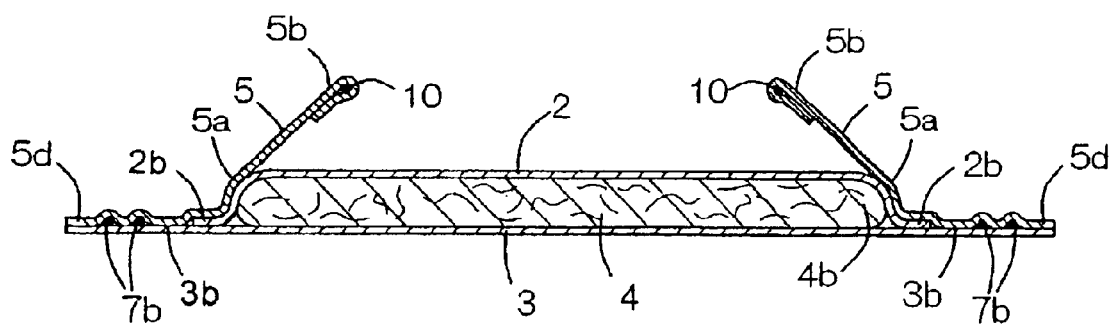
FIG. 5 is a cross-sectional view taken along line V—V of FIG. 1.

FIGS. 3 and 4 are cross-sectional views taken along line III—III and line IV—IV of FIG. 1, respectively. FIG. 5 is a cross-sectional view taken along line V—V of FIG. 1. In each side edge 1a of the diaper 1A, an end 2a of the top sheet and an end 3a of the back sheet 3 extend together outwardly from the side edge 4a of the core 4 where inside surfaces of those ends 2a, 3a are joined to each other, as shown in FIGS. 3 and 4. The waist elastic members 6 and the first auxiliary elastic members 8a are interposed between the top sheet 2 and the back sheet 3 and joined to the respective inside surfaces of the sheets by mean of adhesives (not shown). The second auxiliary elastic members 8b are interposed between the core 4 and the back sheet 3 and joined to the inside surface of the back sheet 3 by mean of adhesives (not shown).

In each of the side edges 1b of the diaper 1A, the side portion 2b of the top sheet 2 is positioned between a side portion 3b of the back sheet 3 and a side portion 5d of the cuff 5 and secured to those portions 3b, 5d, as shown in FIG. 5. The side portions 3b, 5d are secured to each other where they overlap. When the elastic member 10 contracts, the free edge 5b of the cuff 5 is caused to rise from the top sheet 2 to form a barrier against leakage of excrements. The leg elastic members 7 are positioned between the side portion 3b of the back sheet 3 and the side portion 5d of the cuff 5 and secured to those side portions 3b, 5d by means of adhesives (not shown).

Figure 6:
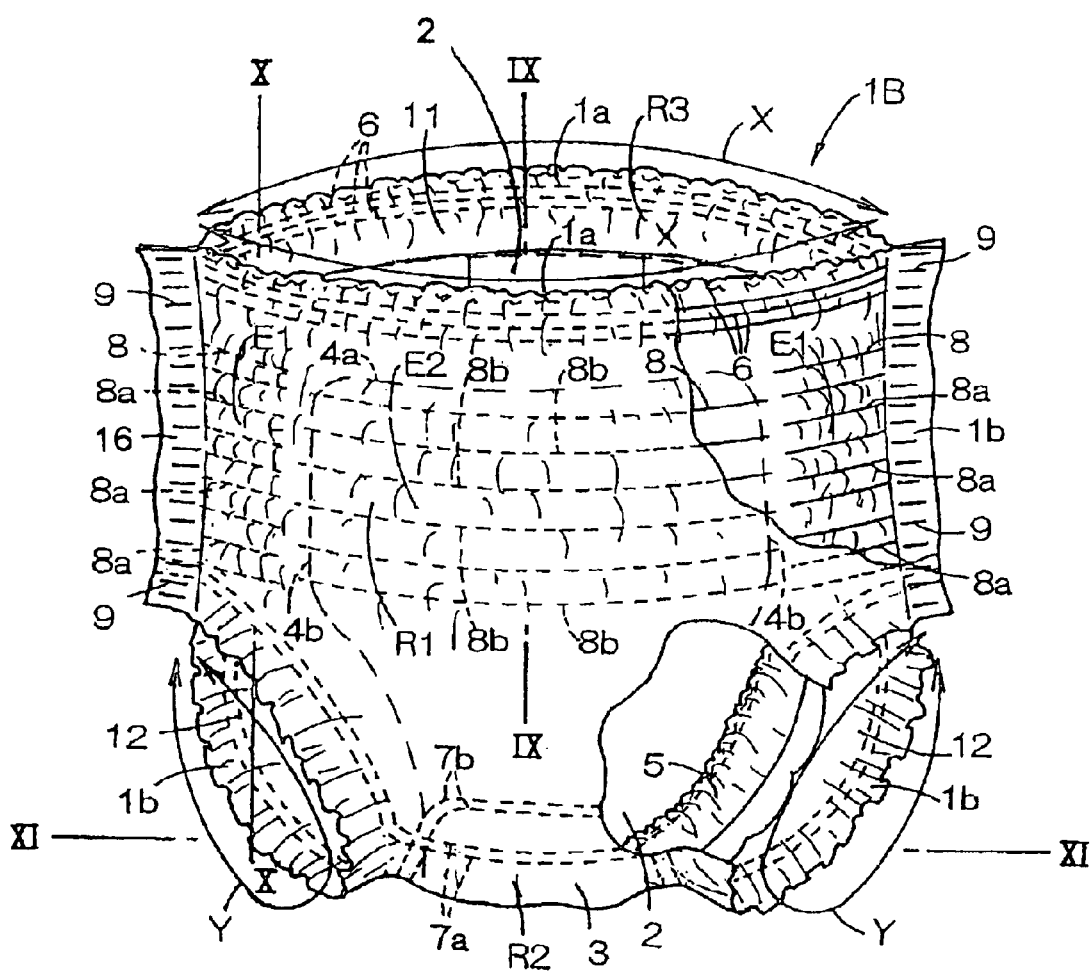
FIG. 6 is a partially cut-away perspective view of a disposable diaper in another exemplary embodiment of the invention.
Figure 7:
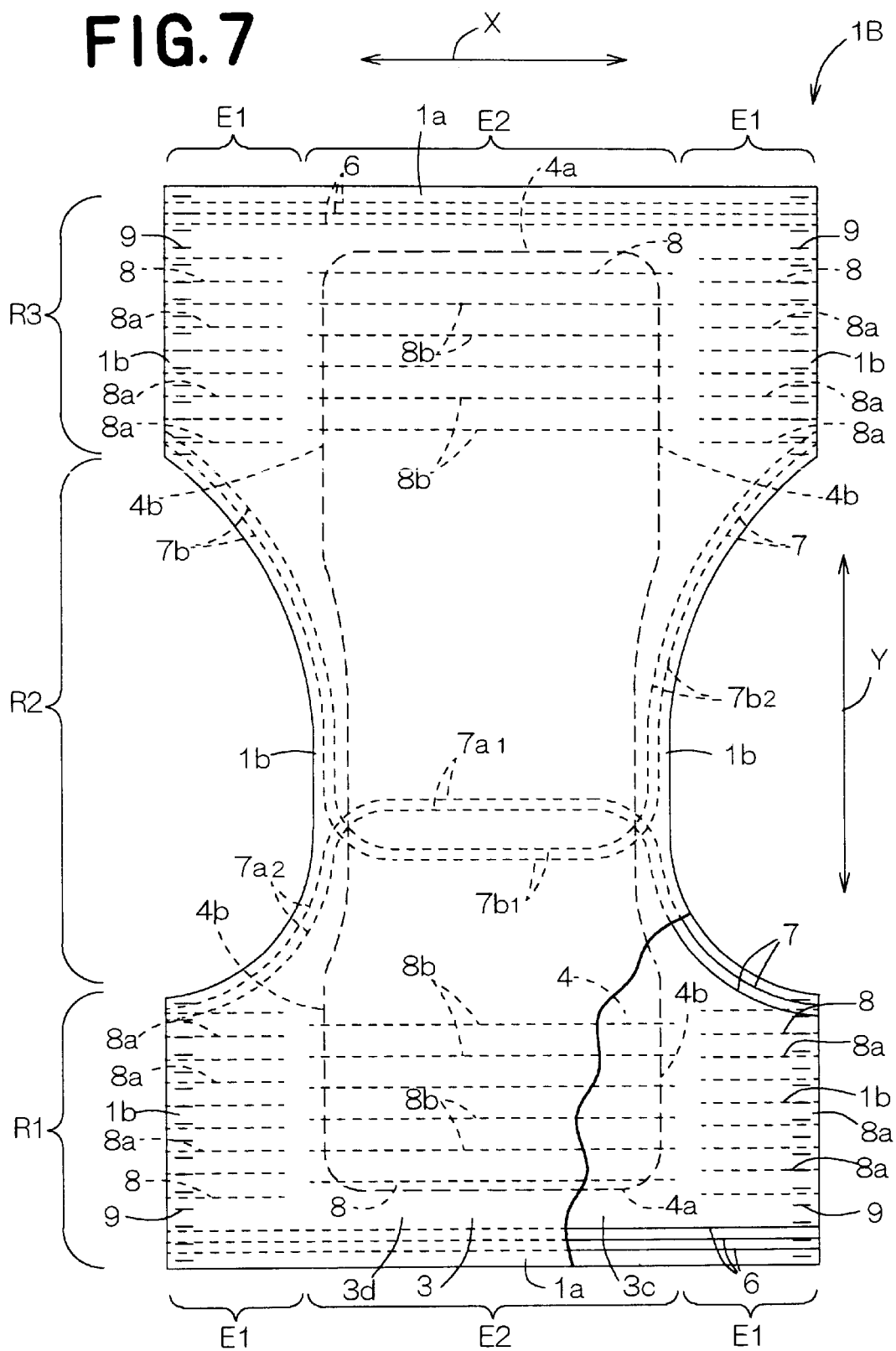
FIG. 7 is a partially cut-away plan view of the diaper when the front and rear waist regions are disconnected from each other and developed longitudinally.
Figure 8:
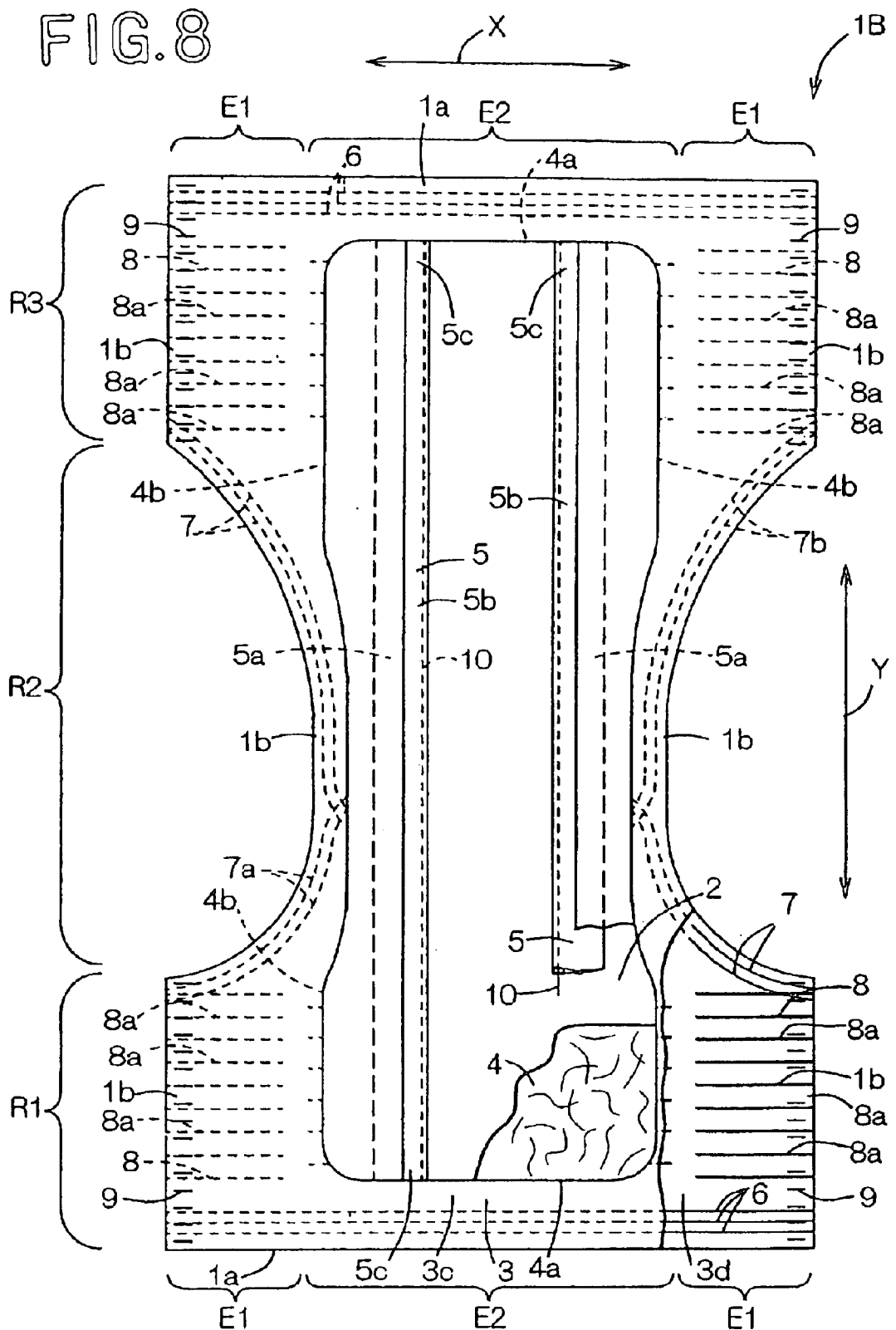
FIG. 8 is a view similar to FIG. 7 as seen from the side of the top sheet.

FIG. 6 is a partially cut-away perspective view of a diaper 1B in accordance with another exemplary embodiment. FIG. 7 is a partially cut-away plan view of the diaper 1B when its front and rear waist-encircling regions R1, R3 are disconnected from each other and developed in a longitudinal direction. FIG. 8 is similar to FIG. 7 but viewed from a side of the top sheet 2. In FIG. 6, a waist-encircling direction and a leg-encircling direction are indicated by the arrows X and Y, respectively. In FIGS. 7 and 8, a lateral direction and a longitudinal direction are indicated by the arrows X and Y, respectively.

The diaper 1B shown in FIG. 6 differs from the diaper shown in FIG. 1 in the following respects. In the diaper 1B, a liquid impervious back sheet 3 is in advance formed into a garment of the pull-on type, and a liquid-absorbing core 4 covered with a liquid pervious top sheet 2 and a water-impervious film 13 is secured to an inner surface of the back sheet 3. The core 4 is enclosed entirely by and joined to tissue paper (not shown). The core is joined via the tissue paper to the inner surfaces of the top sheet 2 and the water-impervious film 13.

As shown in FIG. 7, the diaper 1B has opposite end edges 1a and opposite side edges 1b. Each of the side edges 1b in the crotch region R2 describes a line curved laterally inward of the diaper 1B. In each of the front and rear waist-encircling regions R1 and R3, a plurality of auxiliary elastic members 8 extending laterally and spaced longitudinally from each other by a pre-determined distance are secured in an extended state in a region between the waist elastic members 6 and the leg elastic members 7. The auxiliary elastic members 8 include plural lines of first auxiliary elastic members 8a and plural lines of second auxiliary elastic members 8b.

As shown in FIG. 6, the first auxiliary elastic members 8a are spaced longitudinally from each other by a pre-determined distance and extend in a waist-encircling direction in the first elasticized zones E1. The second auxiliary elastic members 8b are spaced longitudinally from each other by a pre-determined distance and extend in a waist-encircling direction in the second elasticized zone E2. The number of the first auxiliary elastic members 8a is larger than that of the second auxiliary elastic members 8b. The tensile stress of each first auxiliary elastic member 8a is greater than or equal to the tensile stress of each second auxiliary elastic member 8b.

In the diaper 1B, the number of the first auxiliary elastic members 8a is larger than that of the second auxiliary elastic members 8b. Accordingly, even in the case where the tensile stress of each first auxiliary elastic member 8a is comparable to that of each second auxiliary elastic member 8b, each first elasticized zone E1 shows a higher tensile stress than the second elasticized zone E2.

In the diaper 1B, each first elasticized zone E1 when extended to its maximum extent shows a tensile stress in a range of 0.2–2.0 N/25 mm, preferably in a range of 0.4–1.0 N/25 mm, and the second elasticized zone E2 when extended to its maximum extent shows a tensile stress in a range of 0.1–0.6 N/25 mm. The tensile stresses of those elasticized zones E1 and E2 are measured according to the same procedure as applied to the diaper 1A shown in FIG. 1.

The diaper 1B in use tightens around the wearer's waist more strongly in the first elasticized zones E1 than in the second elasticized zone E2. However, the first and second elasticized zones E1 and E2 act in concert with each other to hold the diaper 1B around the wearer's waist and prevent the diaper 1B from sliding down from its intended position. This allows the tensile stress of the first elasticized zones E1 to be within the above-specified range.

In the second elasticized zone E2 of the diaper 1B, the core 4 is pressed against the wearer's skin by the tensile stress of the second auxiliary elastic members 8b so that its excrement-absorbing function is not adversely affected. Since the tensile stress of the second elasticized zone E2 in the diaper 1B is maintained within the above-specified range, the core 4 due to its rigidity withstands the force exerted by the contraction of the second elasticized zone E2 and wrinkles will not be formed on the core 4.

Figure 9:
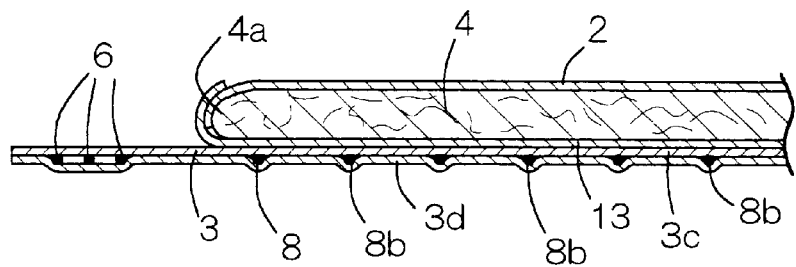
FIG. 9 is a cross-sectional view taken along line IX—IX of FIG. 6.
Figure 10:
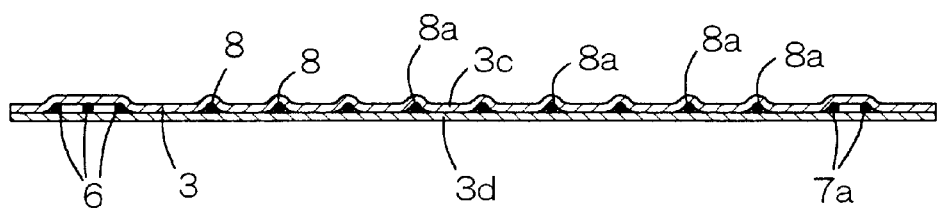
FIG. 10 is a cross-sectional view taken along line X—X of FIG. 6.
Figure 11:
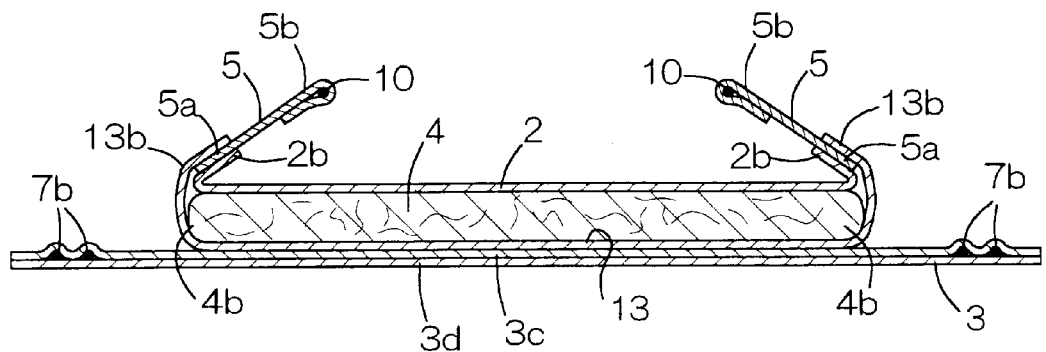
FIG. 11 is a cross-sectional view taken along line XI—XI of FIG. 6.

FIGS. 9 and 10 are cross-sectional views taken along line IX—IX and line X—X of FIG. 6, respectively. FIG. 11 is a cross-sectional view taken along line XI—XI of FIG. 6. The back sheet 3 comprises two mutually overlaid hydrophobic non-woven fabrics 3c and 3d with their opposing surfaces being joined intermittently. The back sheet 3 may comprise a composite sheet made by laminating a hydrophobic non-woven fabric and a plastic film.

Waist elastic members 6, first and second leg elastic members 7a and 7b, and first and second auxiliary elastic members 8a and 8b are all positioned between the non-woven fabrics 3c and 3d constituting the back sheet 3 and secured to those non-woven fabrics 3c, 3d by adhesives (not shown).

In the diaper 1B, a side portion 2b of the top sheet 2 and a side portion 13b of a water-impervious film 13 extend outwardly from each side edge 4b of the core 4, as shown in FIG. 11. The film side portion 13b is folded upwardly from each side edge 4b of the core 4 to overlay an outside surface of the top sheet 2. The fixed edge 5a of each leakage-resistant cuff 5 is located between and secured to the side portions 2b and 13b. The fixed ends 5c of the cuff 5 are both secured to the outside surface of the top sheet 2. The free edge 5b of the cuff 5 rises from the top sheet 2 due to contraction of the elastic member 10.

Non-woven fabrics of hydrophilic fibers and porous plastic films with a large number of micro-pores can be used for the top sheet 2. Non-woven fabrics of hydrophilic fibers, liquid impervious plastic films and laminate sheets comprised of a hydrophilic non-woven fabric and a liquid impervious plastic film can be used for the back sheet 3 of the diaper 1A shown in FIG. 1. Non-woven fabrics of hydrophilic fibers can be used for the leakage-resistance cuff 5. Flexible plastic films can be used for the water-impervious film 13.

A composite non-woven fabric with a highly water-resistant non-woven fabric made by melt-blown process disposed between high-strength and highly flexible spun-bonded non-woven fabrics can also be used for the back sheet 3, 3c, 3d and the cuff 5 of the diaper 1A, 1B shown as embodiments.

Useful non-woven fabrics can be manufactured by various techniques including spun-lacing, needle punching, melt blown, thermal bonding, spun-bonding, chemical bonding, air-through and other processes. Examples of useful fibers constituting such non-woven fabrics include fibers such as of polyolefin, polyester and polyamide, sheath-core and side-by-side conjugate fibers such as of polyethylene/polypropylene or polyester.

The elastic members 6, 7, 8 and 10 are elastomers comprising a natural or synthetic rubber. In the shown diapers 1A, 1B, the elastic members 6, 7, 8 and 10 take the form of strands. However, the elastic members 6, 7, 8 and 10 may take a form of bands.

In the diaper 1A and 1B shown as embodiments, the elastic members 6, 7, 8 and 10 may be secured, either in an intermittent or continuous manner, to the top and back sheets 2, 3, 3c, 3d and the cuff 5 by means of adhesives. Also in the diaper 1A and 1B shown as embodiments, the waist elastic members 6 and the auxiliary elastic members 8 may be attached to at least one of the front and rear waist-encircling regions R1 and R3.

The core 4 comprises a mixture of fluff pulps, high-absorbent polymer particles and thermoplastic synthetic fibers and is provided in the form of being compressed to a pre-determined thickness. Accordingly, the core 4 exhibits higher rigidity compared to the top and back sheets 2, 3, 3c, 3d and the cuff 5. Examples of useful high-absorbent polymers include starch-, cellulose- and synthetic polymer-based polymers.

Hot-melt adhesives or welding means such as sonic sealing or heat sealing can be utilized to secure the top sheet 2 to the back sheet 3, 3c, 3d, secure the leakage-resistant cuff 5 and water-impervious film 13, and join the core 4.

The disposable pull-on garment in the present invention, in use, tightens around the wearer's waist by the tensile stress of the first and second elasticized zones so that the garment can be prevented from sliding down from its intended position. In the garment in which the tensile stress of each first auxiliary elastic member is greater than the tensile stress of each second auxiliary elastic member, and the tensile stress of the first elasticized zones is greater than the tensile stress of the second elasticized zone, the first elasticized zones tighten around the wearer's waist more strongly than the second elasticized zone. However, the first elasticized zones do not function alone but act in concert with the second elasticized zone to tighten the garment around the wearer's waist. Hence, the tensile stress of the first elasticized zones in this garment is not required to be increased to such a high level as required in the prior art garment. As a result, a situation in which the first elasticized zones exert a strong pressure on the wearer's waist can be avoided.

In the garment in which the tensile stress of each first auxiliary elastic member is greater than or equal to the tensile stress of each second auxiliary elastic member, and the number of the first auxiliary elastic members is larger than that of the second auxiliary elastic members, the first elasticized zones exhibit a higher tensile stress than the second elasticized zone and tighten around the wearer's waist more strongly than the second elasticized zone. However, the first elasticized zones do not function alone but act in concert with the second elasticized zone to tighten the garment around the wearer's waist. Hence, the tensile stress of the first elasticized zones in this garment is not required to be increased to such a high level as required for the prior art garment. As a result, a situation in which the first elasticized zones exert a strong pressure on the wearer's waist can be avoided.

Also, in the inventive garments, the core is pressed against the wearer's skin by the tensile stress of the second auxiliary elastic members so that it is prevented from being spaced from the wearer's skin. As a result, a situation in which the excrement-absorbing function of the core is adversely affected can be avoided. Also, in accordance with these inventive garments, the core due to its rigidity withstands the force exerted by the contraction of the second elasticized zone E2 and wrinkles will not be formed on the core. As a result, a situation in which the core is spaced from the wearer's skin can be avoided.

What is claimed is:

1. A disposable pull-on garment having a waist-encirclable direction and a longitudinal direction orthogonal to said waist-encirclable direction, said garment comprising:

a liquid-pervious topsheet, a liquid-impervious backsheet and a liquid-absorbent core interposed between said topsheet and backsheet;

front and real waist-encirclable regions and a crotch region extending between said front and rear waist-encirclable regions;

respective longitudinal side edges of said front and rear waist encirclable regions being joined together in said longitudinal direction to define a waist-encirclable opening and a pair of leg-encirclable openings;

waist-encirclable elastic members attached to respective edge zones of said waist-encirclable opening in said front and rear waist-encirclable regions;

plural lines of auxiliary elastic members which extend in said waist-encirclable direction, and are arranged to be spaced at distances from each other in said longitudinal direction in a region defined between said waist-encirclable elastic members and said leg-encirclable openings in at least one of said front and rear waist-encirclable regions;

said at least one of said front and rear waist-encirclable regions having first elasticized zones and a second elasticized zone, wherein said second elasticized zone traverses a portion of said core in that region and extends in the waist-encirclable direction between opposite longitudinal side edges of said portion of said core, and wherein said first elasticized zones extend in the waist-encirclable direction outwardly from the longitudinal side edges of said portion of said core, respectively, to the adjacent one of the longitudinal side edges of the associated waist-encirclable region;

said auxiliary elastic members including plural lines of first and second auxiliary elastic members, said first auxiliary elastic members being positioned in said first elasticized zones, said second auxiliary elastic members being non-continuous with said first auxiliary elastic members and being positioned in said second elasticized zone; and a tensile stress of said first elasticized zone being greater than that of said second elasticized zone.

2. The garment of claim 1, wherein a tensile stress of said first auxiliary elastic members is greater than that of said second auxiliary elastic members.

3. The garment of claim 1, wherein the number of said first auxiliary elastic members is equal to that of said second auxiliary elastic members.

4. The garment of claim 1, wherein the number of said first auxiliary elastic members is larger than that of the second auxiliary elastic members.

5. The garment of claim 4, wherein a tensile stress of each of said first auxiliary elastic members is greater than or equal to that of each of said second auxiliary elastic members.

6. The garment of claim 4, wherein the first and second auxiliary elastic members are arranged in said longitudinal direction in a staggered manner.

7. The garment of claim 1, further comprising leg-encirclable elastic members being attached to respective edge zones of said leg-encirclable openings.

8. The garment of claim 1, further comprising a pair of leakage-prevention cuffs, each cuff including a fixed edge, and a free edge and extending in said longitudinal direction adjacent one of said longitudinal side edges of said core, wherein said free edge is provided with an elastic member.

9. The garment of claim 8, wherein said garment further comprises leg-encirclable elastic members each extending along an edge of one of said leg-encirclable openings; and each of said leakage-prevention cuffs further includes a side portion extending laterally outwardly from the adjacent longitudinal side edge of said core and being joined onto a respective one of longitudinal side portions of said backsheet each of the leg-encirclable elastic members being disposed between, one of said side portions of said leakage-prevention cuffs and the respective longitudinal side portion of said backsheet, said respective longitudinal side portion of said backsheet also extending laterally outwardly from the adjacent longitudinal side edge of said core.

10. The garment of claim 9, wherein said topsheet has longitudinal side portions each extending laterally outwardly from one of the longitudinal side edges of said core and being positioned between the side portion of the respective one of said leakage-prevention cuffs and the respective one of said longitudinal side portions of said backsheet.

11. The garment of claim 1, further comprising a water-impervious film, wherein said core is interposed between said topsheet and said water-impervious film, said film being secured onto said backsheet, and side portions of said topsheet and said film are joined to each other in said longitudinal direction.

12. The garment of claim 11, wherein said backsheet includes an upper nonwoven fabric and a lower nonwoven fabric, and said waist-encirclable elastic members and said auxiliary elastic members are interposed between said upper and lower nonwoven fabrics.

13. The garment of claim 11, further comprising a pair of leakage-prevention cuffs, each cuff including a fixed edge, and a free edge and extending in said longitudinal direction adjacent one of said longitudinal side edges of said core, wherein said free edge is provided with an elastic member and said fixed edge is placed between respective longitudinal side portions of said topsheet and said film.

14. The garment of claim 1, wherein when each of said first elasticized zones is extended to a maximum extent, said first elasticized zone exhibits a tensile stress in a range of 0.2–2.0 N/25 mm; and when said second elasticized zone is extended to a maximum extent, said second elasticized zone exhibits a tensile stress in a range of 0.1–0.6 N/25 mm.

15. The garment of claim 1, wherein a tensile stress of each of said first auxiliary elastic members is greater than that of each of said second auxiliary elastic members.

16. The garment of claim 1, wherein the auxiliary elastic members are spaced at equal intervals in said longitudinal direction.

17. The garment of claim 1, wherein each of said front and rear waist-encirclable regions includes first elasticized zones and a second elasticized zone.

* * * * *